US008656920B1

(12) United States Patent
Tannatt

(10) Patent No.: US 8,656,920 B1
(45) Date of Patent: Feb. 25, 2014

(54) DEVICE TO ALLEVIATE SNORING

(76) Inventor: Theresa Tannatt, Sherman Oaks, CA (US)

(*) Notice: Subject to any disclaimer, the term of this patent is extended or adjusted under 35 U.S.C. 154(b) by 333 days.

(21) Appl. No.: 12/928,643

(22) Filed: Dec. 17, 2010

(51) Int. Cl.
*A61F 5/56* (2006.01)
*A61C 3/00* (2006.01)

(52) U.S. Cl.
USPC ................................. 128/848; 433/6

(58) Field of Classification Search
USPC ............ 128/848, 859–862; 602/902; 433/6–7
See application file for complete search history.

(56) References Cited

U.S. PATENT DOCUMENTS

| 4,815,968 | A | * | 3/1989 | Keller | 433/7 |
| 5,052,409 | A | * | 10/1991 | Tepper | 128/859 |
| 5,865,619 | A | * | 2/1999 | Cross et al. | 433/6 |
| 6,332,774 | B1 | * | 12/2001 | Chikami | 433/20 |

* cited by examiner

*Primary Examiner* — Patricia Bianco
*Assistant Examiner* — Ophelia A Hawthorne
(74) *Attorney, Agent, or Firm* — Kelly & Kelley, LLP

(57) ABSTRACT

A device to alleviate snoring is disclosed. It is an appliance that fits into the mouth, is held against the roof of the mouth by means on the upper premolars, and presses against the soft palate, preventing the soft palate from descending into the airway of the user.

4 Claims, 3 Drawing Sheets

DEVICE TO ALLEVIATE SNORING

Snoring is a common affliction. Snoring is caused by blockage of the air passage way during sleep, involving the soft palate and uvula. More specifically, the soft palate descends during sleep to partially block the airway. That descent can be produced or aggravated by many different factors. For instance, by relaxation of the soft palate support caused by sleep itself. Other causes include overweight, sleeping on the back, and a mispositioned jaw.

Snoring can signify sleep apnea, produce daytime fatigue, cause headaches, irritate partners, and cause irritability—among other negative symptoms.

It is therefore desirable to produce a device to minimize or stop snoring.

PRIOR ART

Many methods and devices have been, and are being, set forth as remedies for snoring.

Among these are appliances to advance the lower mandible, nasal sprays, nasal strips. More aggressive methods include the use of a positive air pressure breathing machine (CPAP), and in extreme cases, pharnygeal surgery. Each of these methods or devices has its advantages and disadvantages. Surgery, for instance, may not work, and can even produce worsening of the snoring problem, due to the formation of scar tissue in the air passageway. The CPAP machine is bulky, difficult to transport, and expensive. The appliance to advance the lower mandible requires a prescription, and can produce jaw pain. The nasal sprays, while lessening the problem of snoring, typically do not solve it. Similar limited success is found with nasal strips. Hence, it is desirable to provide a device that alleviates snoring while being portable, adjustable by the individual user, and inexpensive.

BRIEF DESCRIPTION OF THE INSTANT INVENTION

The invention described and claimed herein can be described as an oval shaped non-elastic bendable appliance that is fitted by the user or a professional health provider to the roof of the user's mouth. It is held in place by, for instance, press fit clamps securing it to two teeth on opposite sides of the upper mandible, typically the teeth just behind the canine or eye teeth, as the premolars provide maximum support and easy access. When in place, the device is parallel to the upper mandible's teeth.

DETAILED DESCRIPTION OF THE INVENTION

It should be understood that the embodiment pictured is that of the basic device of the invention. For instance, it is illustrated with insulated solid wires. While functional, that is not the only embodiment possible. Various modifications of the invention may be made without departing from the spirit and scope of the invention. Accordingly, the invention is not to be limited, except as by the appended claims.

Figure 1:
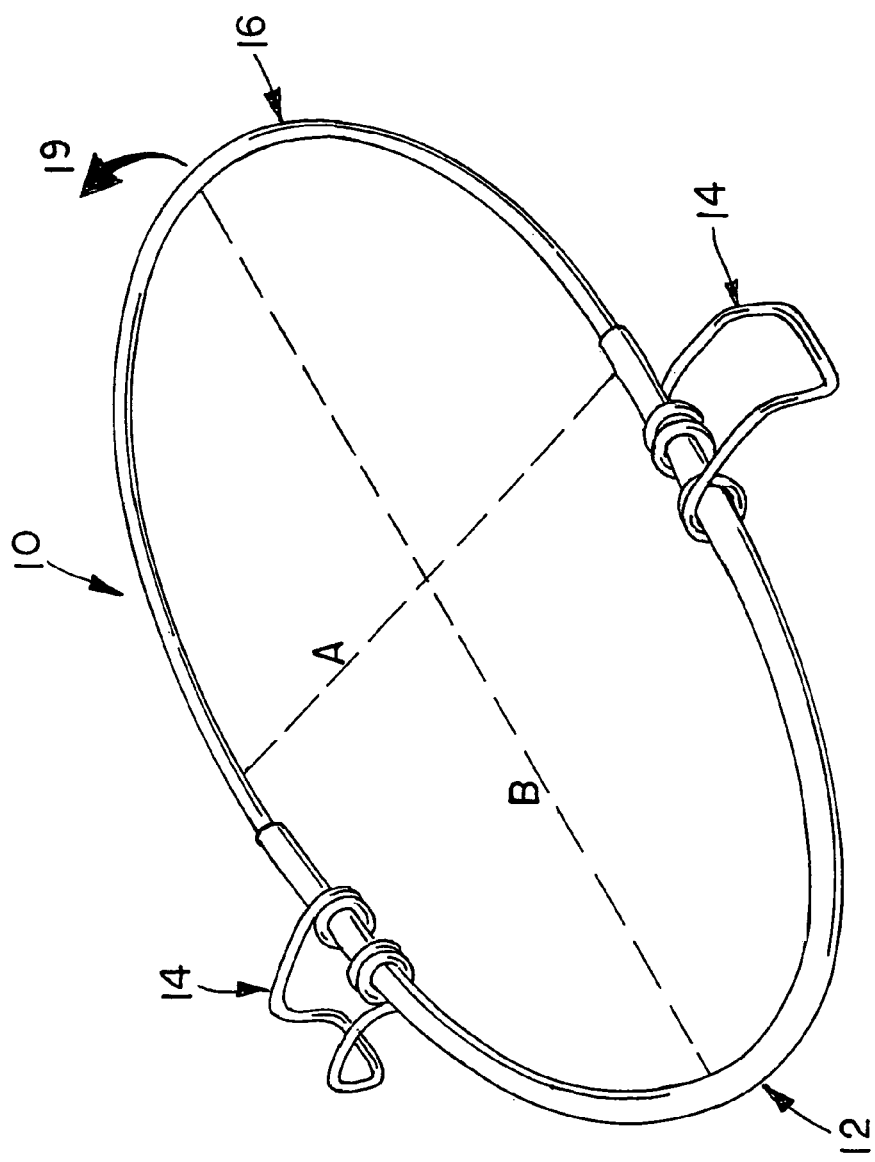
FIG. 1 is a top perspective view of the device of the instant invention.

Referring now to the Figures, an assembled device is shown in FIG. 1. It comprises a rear "U" shaped bendable non-elastic support rod 16. That rear portion, while flexible, will retain the shaped into which it bent or flexed, much like a solid wire. In other words, it is non-elastic. In use, it serves to prevent the soft palate from descending. The two forward arms of the rear portion 16 are slip fitted into a the two rearward pointed "U" shaped bendable non-elastic flexible bridge tube 12. The slip fit allows for adjustment of the length of the device to suit the user. In one configuration, Inside the tube 12 a stiffener (Shown in FIG. 2) 18 causes the tube to hold a configuration into which it is bent. In another configuration, the tube itself is stiff enough to be non-elastic, but bendable. It can be seen that the assembly can therefore be bent into a narrower or wider configuration to suit the user. The device also has a plurality of fastening means, in this case two clamps 14 slidably affixed to the tube 12. In use, the clamps are a press fit on the tooth behind the canine tooth, thereby holding the device at or near the roof of the user's mouth. In the embodiment shown, the outer arm 15 contacts the outer surface of the user's tooth, while the inner portion 17 of the clamp contacts the inner surface of the tooth. The clamp operates by being "springy", that is, being sprung such that the outer arm 15 tends to approach the inner portion 17, thereby squeezing the tooth, and being removably affixed to the tooth thereby. This is also illustrated in FIG. 3. The slidable nature of the clamps 14, again, is to allow the adjustment of the device for the individual user.

It should be understood that while the embodiment shown is of the "one size fits all" fashion, due to its multiple adjustments, that configuration is not required. If a device of the instant invention is made of, for instance, thermo-setting plastic, it can be fitted to the individual user, and then be fixed in that configuration, in a fashion known to those in the art.

Figure 2:
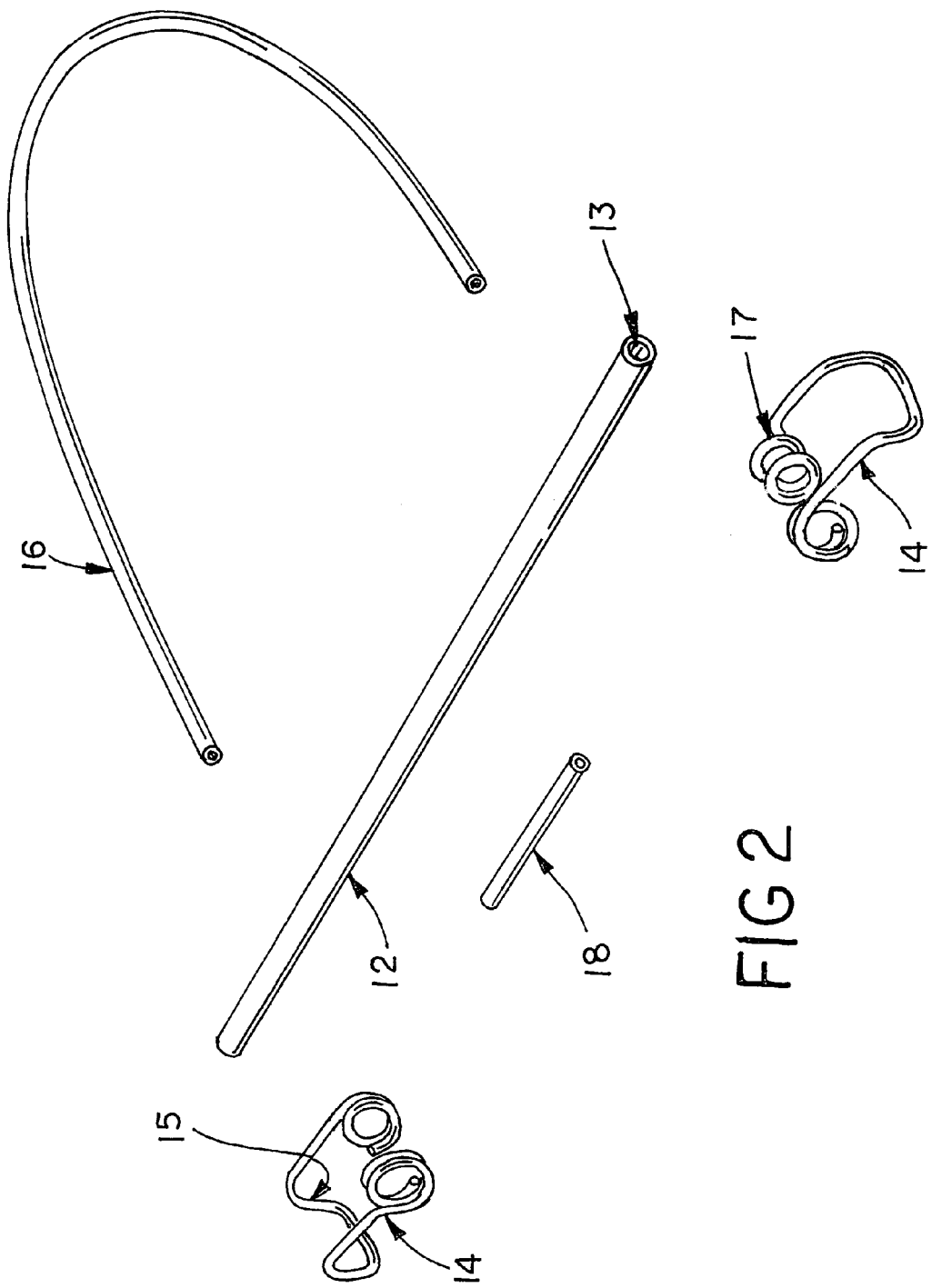
FIG. 2 is an exploded view of the device of the instant invention.
Figure 3:
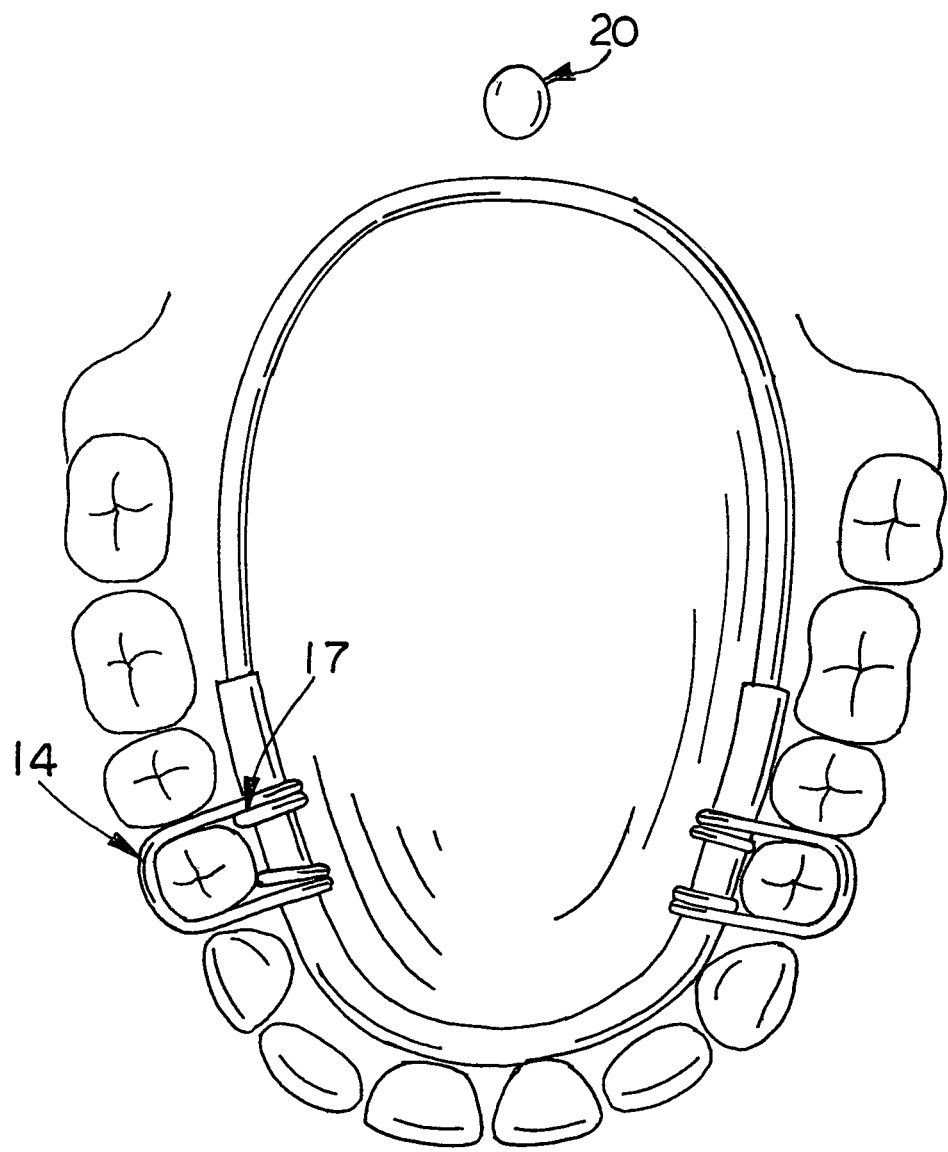
FIG. 3 is a bottom view of the roof of the mouth with the device in place.

Referring to FIG. 2, the device is shown in an exploded view. In this view, the tube stiffener 18 is visible. When the device is assembled, the stiffener 18 is inserted into the tube 12 through an orifice 13 at either end of the tube 12. Then, the clamps 14 are slid onto the bridge tube, and finally the arms of the rear portion 16 are inserted into their respective orifices 13 at either end of the tube 12.

Referring now to FIG. 3, the device is shown in its position of the roof of of the user's mouth. It can be seen that the clamps are affixed to the teeth behind the canine teeth. Further, the device has been squeezed along its length, so that its minor axis A (FIG. 1) fits between the teeth. Similarly, the rear portion 16 has been slid the proper distance inside the tube 13 such that the major axis B (FIG. 2) of the device places the rearmost portion of the rear portion either behind the uvula, or just in front of it.

Referring back to FIG. 1, the device is illustrated to be planar. In use it is not. Rather, the rear of the rear portion 12 is bent upward in the direction of the arrow 19, and retains that bend. Thus, the entire device except the rearmost portion is in a plane along the roof of the mouth, but the bending of the rear causes it to be higher, pressing the portion of the roof of the mouth just in front or just behind the uvula upwards. This upwards pressing stops the soft palate from descending and partially blocking the air passage. It is that partial blocking that is the cause of many types of snoring, and stopping that blockage alleviates the snoring.

I claim:

1. A device for alleviating snoring, comprising:
a front bridge tube being bendable and non-elastic, configured in a "U" shape having a front apex and two rearward facing arms;

a "U" shaped rear support rod being bendable and non-elastic, having a rear apex and two forward facing arms, wherein the rear apex is bent upwards and configured for disposal proximate to a uvula, with the two forward facing arms slip fitted in the two rearward facing arms of the front bridge tube; and at least two fastening means disposed on the two rearward facing arms and configured to fasten the device to one or more teeth on an upper mandible, with the front bridge tube and part of the rear support rod configured to be disposed in a plane generally parallel to the upper mandible, and the rear apex adapted to extend upwards into a soft palate.

2. The device of claim 1, wherein the support rod comprises a coated solid wire.

3. The device of claim 1, wherein the at least two fastening means comprise a pair of resilient clamps configured for being press-fit onto teeth on the upper mandible.

4. The device of claim 1, wherein the front bridge tube has a bendable non-elastic member inserted therein and disposed at the front apex.

* * * * *